United States Patent [19]

Yamanishi et al.

[11] Patent Number: 4,592,996
[45] Date of Patent: Jun. 3, 1986

[54] PROCESS FOR DETERMINING REDUCED FORM COENZYMES

[75] Inventors: Kazuhiko Yamanishi, Tokyo; Toshiro Hanada, Kawagoe, both of Japan

[73] Assignee: Wako Pure Chemical Industries, Ltd., Osaka, Japan

[21] Appl. No.: 608,681

[22] Filed: May 10, 1984

[30] Foreign Application Priority Data

May 10, 1983 [JP] Japan .................... 58-81153

[51] Int. Cl.$^4$ .............. C12Q 1/60; C12Q 1/32; C12Q 1/28; C12N 9/96
[52] U.S. Cl. ........................... 435/11; 435/26; 435/28; 435/188
[58] Field of Search ............... 435/4, 11, 26, 28, 188

[56] References Cited

U.S. PATENT DOCUMENTS 3,791,933  2/1974  Moyer et al. ............... 435/28
4,186,052  1/1980  Röder et al. ............... 435/28
4,310,626  1/1982  Burkhardt et al. ........... 435/28
4,331,761  5/1982  Dawson et al. ............. 435/28
4,394,444  7/1983  Cameron et al. ........... 435/28

FOREIGN PATENT DOCUMENTS 157894  12/1979  Japan ...................... 435/26

OTHER PUBLICATIONS

Swedin et al., Nature 145, 71-72 (1940).

*Primary Examiner*—Esther M. Kepplinger
*Attorney, Agent, or Firm*—Armstrong, Nikaido, Marmelstein & Kubovcik

[57] ABSTRACT

A reduced form coenzyme can be determined by acting a peroxidase on a reduced form coenzyme in the presence of metal ions to generate hydrogen peroxide and measuring the amount of hydrogen peroxide colorimetrically.

12 Claims, 5 Drawing Figures

PROCESS FOR DETERMINING REDUCED FORM COENZYMES

This invention relates to a process for determining a reduced form coenzyme. More in detail, this invention relates to a process for determining a reduced form coenzyme by quantitatively oxidizing a reduced form coenzyme by enzymatic action of peroxidase in the presence of metal ions preferably divalent manganese ions and/or divalent cobalt ions to produce an oxidized form coenzyme and hydrogen peroxide, said reduced form coenzyme either being present in a sample to be determined such as body fluid or being obtained from a substrate through necessary reactions, and measuring the amount of hydrogen peroxide colorimetrically by a conventional method.

To measure enzymatic activities or amounts or concentrations of substances (substrates) in a living sample such as body fluid is very important for diagnosis of diseases, effects on remedy or mechanism of diseases.

It is general to use a coenzyme in order to exhibit the action of a dehydrogenase, in the case of measuring the activity of a dehydrogenase such as lactate dehydrogenase (LDH), and α-hydroxybutyrate dehydrogenase (α-HBD), which are present in a body fluid such as serum, urine, or the like, used as a test sample, in the case of measuring the activity of other enzyme in a test sample by interposing such a dehydrogenase, or in the case of determining the amount of substance (substrate) in a test sample in the presence of a dehydrogenase which specifically acts on the substance (substrate) such as cholesterol, triglyceride, glucose, formaldehyde, aldehydes, bile acids, or the like. These coenzymes are transformed by the action of a dehydrogenase to reduced form coenzymes, which are determined in order to know the enzymatic activity or the amounts of substrates in the test sample.

As the reduced form coenzymes, there are usually used nicotinamide adenine dinucleotide, reduced form (hereinafter referred to as "NADH") and nicotinamide adenine dinucleotidephosphate, reduced from (hereinafter referred to as "NADPH"). In the case of determining NADH or NADPH which are typical reduced form coenzymes, it has been general that absorbance at 340 nm is measured or NADH or NADPH is reacted with a tetrazolium compound to give a colored formazan which is colorimetrically determined in the visible region. But in the case of measuring absorbance at 340 nm, since the absorbance is influenced by a substance, which is present in the sample and has an absorption at a lower wavelength side, such as bilirubin, hemoglobin, or the like, it is necessary to measure blank values of the sample and to use a special apparatus for measuring ultraviolet absorption. In the case of the visible color producing method using the tetrazolium compound, since the colored formazan produced by the reaction of the reduced form coenzyme with the tetrazolium compound is low in solubility in the water and strong in staining properties, the dye produced often precipitates and deposits, or stains a cuvette or tube, which results in becoming serious defects for the measurement.

On the other hand, there are various kinds of redox color reagents with different oxidation-reduction potentials, with different solubilities in water, with different colors to be produced, and with different staining properties, so that it is possible to select a suitable one depending on the purposes. Further, the redox color reagents can easily be colored quantitatively by hydrogen peroxide with peroxidase. If hydrogen peroxide can quantititively generated from a reduced form coenzyme, since the hydrogen peroxide thus generated can produce color quantitatively from the redox color reagents, it becomes possible to determine the reduced form coenzyme overcoming the defects of the prior art methods.

It is generally known that a peroxidase is an enzyme which catalyzes the oxidation reaction using hydrogen peroxide as oxidizing agent. For example, a substrate (YH$_2$) such as dihydroxymaleic acid produces hydrogen peroxide by the action of a peroxidase in the presence of a very small amount of hydrogen peroxide as follows:

$$YH_2 + O_2 \xrightarrow{\text{peroxidase}} Y + H_2O_2$$

the above-mentioned reaction can be accelerated by Mn$^{2+}$ or a phenol (Osamu Hayaishi and Koyo Nozaki: "Oxygen Addition Enzymes" pp. 183–184, (1973), 1st edition, The University of Tokyo Publishing Society; Nature 145, 71-2 (1940)). But in the above-mentioned reaction, since the peroxidase is also present, the hydrogen peroxide produced is partly consumed for oxidizing unreacted YH$_2$. Further, since a small amount of hydrogen peroxide is necessary for starting the reaction, it has been considered difficult to apply this reaction to determination. In addition, there has been no study on applying the above-mentioned reaction to determination of reduced form coenzymes such as NADH and NADPH.

It is an object of this invention to provide a process for determining reduced form coenzyme without using hydrogen peroxide for starting the reaction and measuring only the hydrogen peroxide generated colorimetrically.

This invention provides a process for determing a reduced form coenzyme which comprises acting a peroxidase on a reduced form coenzyme in the presence of metal ions to generate hydrogen peroxide, and measuring the amount of hydrogen peroxide colorimetrically.

In the attached drawings.

When a reduced form coenzyme such as NADH or NADPH is reacted with a peroxidase in the presence of metal ions such as Mn$^{2+}$ or Co$^{2+}$ without adding hydrogen peroxide thereto, hydrogen peroxide is generated. When there are present redox color reagents, the hydrogen peroxide oxidizes the redox color reagents to produce a color, which shows an absorbance in proportion to the concentration of NADH or NADPH. But when no metal ions are present in this system, the generation of hydrogen peroxide can be admitted by the reaction of the peroxidase and the reduced form coenzyme such as NADH or NADPH but the amount of hydrogen peroxide generated is not quantitative. Therefore, the metal ions play the most important and decisive role for generating hydrogen peroxide quantitatively in the process of this invention. On the other hand, phenols do not show accelerating effect on the reaction contrary to the case of substrate such as dihydroxymaleic acid.

The process of this invention can be applied to not only a reduced form coenzyme present in a sample but also a reduced form coenzyme obtained by acting a dehydrogenase on a substrate in the presence of a coenzyme. Therefore, the process of this invention can be applied to a system including such a coenzyme, substrate and dehydrogenase, and enzymes, coenzymes and substrates which can be connected to such a system can also be determined with easy.

Examples of the reduced form coenzyme are NADH and NADPH.

Examples of the metal ions are divalent manganese ions ($Mn^{2+}$), divalent cobalt ions ($Co^{2+}$), and other metal ions having the same function as $Mn^{2+}$ and $Co^{2+}$. These ions can be used alone or as a mixture thereof.

Examples of compounds yielding the metal ions are inorganic acid salts of metals such as chlorides, sulfates, nitrates of manganese, cobalt, etc.; organic acid salts of metals such as acetates, citrates, tartrates, ethylenediamine tetracetates of manganese, cobalt etc. Other compounds which can produce the desired metal ions can also be used in this invention.

The concentration of metal ions is usually 0.1 mmole/l to 200 mmole/l, preferably 0.1–100 mmole/l in the case of $Mn^{2+}$ and 1–200 mmole/l in the case of $Co^{2+}$.

The thus quantitatively generated hydrogen peroxide is measured colorimetrically by a conventional method. For example, a color produced by reacting hydrogen peroxide with redox color reagent or reagents can be measured. Examples of the redox color reagent reagents are a combined system of 4-aminoantipyrine and a phenol series compound, a naphthol series compound or an aniline series compound; a combined system of 3-methylbenzothiazolinonethydrazone (MBTH) and an aniline series compound; 2,2'-azinobis(3-ethylbenzothiazoline-6-sulfonic acid) (ABTS); leucomethylene blue derivatives, etc.

Examples of the phenol series compounds are phenol, p-chlorophenol, 2,4-dichlorophenol, p-bromophenol, o-chlorophenol, m-chlorophenol, etc.

Examples of aniline series compounds are aniline, N,N-dimethylaniline, N,N-diethylaniline, N,N-diethyl-m-toluidine, 3-methyl-N-ethyl-N-(β-hydroxyethyl)aniline, N-ethyl-N-(2-hydroxy-3-sulfopropyl)-m-toluidine, 3,5-dimethyl-N-ethyl-N-(2-hydroxy-3-sulfopropyl)aniline, 3,5-dimethoxy-N-ethyl-(2-hydroxy-3-sulfopropyl)aniline, etc.

Examples of naphthol series compounds are 1-naphthol, 1-naphthol-2-sulfonic acid, 1-naphthol-2-carboxylic acid, 1-naphthol-8-sulfonic acid, 1-naphthol-3-sulfonic acid, 1-naphthol-5-sulfonic acid, etc.

There can also be used, other than those mentioned above, highly sensitive redox color reagents such as triphenylmethane derivatives, e.g. leuco dyes—Leucomalachite Green, Leucocrystal Violet, etc., newly developed bis(p-diethylamino)phenyl 2-sulfophenylmethane, etc.

In addition to the color producing method by using these redox color reagents for determination of hydrogen peroxide, there can be employed a determination method of hydrogen peroxide by using chemical luminescence. That is, when a luminous reagent system comprising a peroxidase and luminol is added to a sample containing hydrogen peroxide, there takes place a luminescence phenomenon as shown below, wherein the peroxidase acts as a catalyst:

The light emitted is photoelectrically transformed into electric signals by using a photo multiplier or the like, and the amount of light can be measured electrically with high accuracy and high speed from the electric signals taken out wherein the electric power is in proportion to the amount of hydrogen peroxide.

The process of this invention can be applied to a single reagent process wherein there take place simultaneously the generation of hydrogen peroxide and the color production by the reaction of the hydrogen peroxide with a redox color reagent system in a single reagent solution containing the redox color reagent system, metal ions and peroxidase, whereby a reduced form coenzyme is determined.

The process of this invention can also be applied to a double reagent process wherein a test sample is added with a first solution containing, for example, metal ions and redox color reagent or reagents but not peroxidase, and incubated, and then is added with a second solution containing only a peroxidase and incubated, followed by colorimetrical determination of the color produced. In the double reagent process, the first solution may contain metal ions and a peroxidase and the second solution may contain redox color reagent or reagents and, if necessary, a peroxidase. There may be employed various variations in the combination of the metal ions, the peroxidase, and the redox color reagent or reagents depending on the purposes.

The process of this invention is explained in more detail in the case of quantitative determination of NADH and NADPH which are typical reduced form coenzymes.

In the case of single reagent process, a color reagent can be prepared by using 0.05M tris-HCl buffer solution (pH 7.5) containing 5 mmole/l. of $MnCl_2.4H_2O$, 6000 units/l of peroxidase (POD), 0.08% by weight of phenol and 0.008% by weight of 4-aminoantipyrine. To 50 μl of a sample solution containing 0.2 to 20 mmole/l of NADH or NADPH, 4 ml of the color reagent is added and incubated at 37° C. for 10 minutes. Then absorbance at 505 nm is measured by using reagent blank as control.

When the double reagent process is employed by using an autoanalyzer, a first solution is prepared by adding 25 mmole/l of $MnCl_2.4H_2O$ and 6000 units/l of POD to 0.05M tris-HCl buffer solution (pH 7.5), and a second solution is prepared by adding 0.1% by weight of phenol, 0.01% by weight of 4-aminoantipyrine and 6000 units/l of POD to 0.05M tris-HCl buffer solution (pH 7.5). To 50 μl of the same sample solution as mentioned above, 1 ml of the first solution is added and incubated at 37° C. for 5 minutes, followed by addition of 3 ml of the second solution and incubation at 37° C. for 10 minutes. Then absorbance at 505 nm is measured by using reagent blank as control.

Needless to say, $H_2O_2$-POD system can also be used as redox color reagent(s) in place of the 4-aminoantipyrine and phenol system. When 4-aminoantipyrine and 3-methyl-N-ethyl-N-($\beta$-hydroxyethyl)aniline system is used as redox color reagent(s), the absorbance is measured at 550 nm, and when 3-methyl-2-benzothiazolinonehydrazone and chromotropic acid system is used, the absorbance is measured at 570 nm.

The pH of the solution used for the reaction is usually 6 to 9, and preferably 6.5 to 8.5 in most cases. When the pH is higher than 7.5, metal ions such as divalent manganese ions, divalent cobalt ions, and the like sometimes precipitate as hydroxides or basic compounds. In such a case, EDTA, a tartrate or a citrate is added to prevent precipitation.

In order to maintain the pH of the solution at a desired value during the reaction, a conventional buffer solution is used. Examples of the buffer solution are a phosphate buffer solution, a tris-HCl buffer solution, a borate buffer solution, and the like. When a phosphate buffer solution is used, it is preferable to add a chelating agent such as EDTA in order to prevent the precipitation of $Mn^{2+}$ as manganese phosphate.

The process of this invention can also be applied to enzymatic reactions wherein a substrate is acted with a dehydrogenase in the presence of a coenzyme to yield a reduced form coenzyme quantitatively. Examples of the dehydrogenase are lactate dehydrogenase (LDH) and $\alpha$-hydroxy butyrate dehydrogenase ($\alpha$-HBD). Examples of the coenzyme are nicotinamide adenine dinucleotide, oxidized form (hereinafter referred to as "NAD") and nicotinamide adenine Dinucleotide-phosphate, oxidized form (hereinafter referred to as "NADP"). Examples of the substrate are lactic acid or $\alpha$-hydroxybutyric acid. Examples of such reactions are as follows:

[Measurement of Activity of LDH]

$$\underset{\text{(lactic acid)}}{\underset{\substack{|\\COOH}}{\overset{\substack{CH_3\\|}}{H-C-OH}}} + NAD \underset{}{\overset{LDH}{\rightleftarrows}} \underset{\text{(pyruvic acid)}}{\underset{\substack{|\\COOH}}{\overset{\substack{CH_3\\|}}{C=O}}} + NADH + H^+$$

$$NADH + \tfrac{1}{2} O_2 \xrightarrow[\text{peroxidase}]{Mn^{2+} \text{ or } Co^{2+}} NAD + \tfrac{1}{2} H_2O_2$$

First Reagent:

| | |
|---|---|
| buffer solution* (pH 7.5–8.5) | 0.5 ml |
| NAD | 0.2–2 g/l |
| L-lactic acid | 1–200 mmole/l |

Second Reagent:

| | |
|---|---|
| buffer solution* (pH 5–6.5) | 3 ml |
| $MnCl_2.4H_2O$ or | 0.1–100 mmole/l |
| $CoCl_2.6H_2O$ | 1–200 mmole/l |
| peroxidase | 500–20000 units/l |
| 4-aminoantipyrine | 0.003–0.03% |
| phenol derivative, aniline derivative, or naphthol derivative | 0.03–0.3% |

*e.g., phosphate buffer, tris buffer, Good's buffer, etc. The generated $H_2O_2$ is measured quantitatively.

[Measurement of Activity of $\alpha$-HBD]

$$\underset{\text{($\alpha$-hydroxybutyric acid)}}{\underset{\substack{|\\COOH}}{\overset{\substack{CH_3\\|\\CH_2\\|}}{H-C-OH}}} + NAD \underset{}{\overset{\alpha\text{-HBD}}{\rightleftarrows}} \underset{\text{($\alpha$-ketobutyric acid)}}{\underset{\substack{|\\COOH}}{\overset{\substack{CH_3\\|\\CH_2\\|}}{C=O}}} + NADH + H^+$$

$$NADH + \tfrac{1}{2} O_2 \xrightarrow[\text{peroxidase}]{Mn^{2+} \text{ or } Co^{2+}} NAD + \tfrac{1}{2} H_2O_2$$

First Reagent:

| | |
|---|---|
| buffer solution* (pH 7.5–8.5) | 0.5 ml |
| NAD | 0.2–2 g/l |
| $\alpha$-hydroxybutyric acid | 1–200 mmole/l |

Second Reagent:

| | |
|---|---|
| buffer solution* (pH 5–6.5) | 3 ml |
| $MnCl_2.4H_2O$ or | 0.1–100 mmole/l |
| $CoCl_2.6H_2O$ | 1–200 mmole/l |
| peroxidase | 500–20000 units/l |
| 4-aminoantipyrine | 0.003–0.03% |
| phenol derivative, aniline derivative, or naphthol derivative | 0.03–0.3% |

*e.g., phosphate buffer, tris buffer, Good's buffer, etc. The generated $H_2O_2$ is measured quantitatively.

The process of this invention can also be applied to enzymatic reactions wherein the substrate is cholesterol, bile acids, glycerol, glycerol-3-phosphate, glucose-6-phosphate, or aldehyde, e.g. formaldehyde, acetaldehyde; the coenzyme is NAD or NADP; and the dehydrogenase is cholesterol dehydrogenase, 3$\alpha$-hydroxysteroid dehydrogenase, glycerol dehydrogenase, glycerol-3-phosphate dehydrogenase, glucose-6-phosphate dehydrogenase, formaldehyde dehydrogenase or aldehyde dehydrogenase; and a substrate is acted with a dehydrogenase in the presence of a coenzyme.

[Measurement of Cholesterol]

$$\text{cholesterol} + NAD \xrightarrow{\text{cholesterol dehydrogenase}} \Delta^4\text{-cholestenon} + NADH + H^+$$

$$NADH + \tfrac{1}{2} O_2 \xrightarrow[\text{peroxidase}]{Mn^{2+} \text{ or } Co^{2+}} NAD + \tfrac{1}{2} H_2O_2$$

Reagent:

| | |
|---|---|
| buffer solution* (pH 6–8) | 3 ml |
| $MnCl_2.4H_2O$ or | 0.1–100 mmole/l |
| $CoCl_2.6H_2O$ | 1–200 mmole/l |
| peroxidase | 500–20000 units/l |
| cholesterol dehydrogenase | 500–5000 units/l |
| NAD | 0.2–2 g/l |
| 4-aminoantipyrine | 0.003–0.03% |
| phenol derivative, aniline derivative, or naphthol derivative | 0.03–0.3% |
| surface active agent (Triton X-100)** | 0.05%–0.2% |

[Measurement of Cholesterol] -continued

| | |
|---|---|
| EDTA-2Na | 0.1–100 mmole/l |

*e.g. tris buffer, phosphate buffer, Good's buffer, etc. The generated $H_2O_2$ is measured quantitatively.
**Triton X-100 is a polyoxyethylene derivative belonging to a class of octylphenyl ether manufactured by Rohm and Haas Co.

[Measurement of Bile Acids]

$$3\alpha\text{-hydroxysteroid} + \text{NAD(P)} \xrightleftharpoons{3\alpha\text{-HSD}} \text{3-oxosteroid} + \text{NAD(P)H} + H^+$$

$$\text{NAD(P)H} + \tfrac{1}{2} O_2 \xrightarrow{\frac{Mn^{2+} \text{ or } Co^{2+}}{\text{peroxidase}}} \text{NAD(P)} + \tfrac{1}{2} H_2O_2$$

$3\alpha$-HSD = $3\alpha$-hydroxysteroid dehydrogenase

Reagent:
| | |
|---|---|
| buffer solution* (pH 6–8.5) | 3 ml |
| $MnCl_2\cdot 4H_2O$ or | 0.1–100 mmole/l |
| $CoCl_2\cdot 6H_2O$ | 1–200 mmole/l |
| peroxidase | 500–20000 units/l |
| 3α-hydroxysteroid dehydrogenase (3α-HSD) | 50–1000 units/l |
| NAD | 0.2–2 g/l |
| 4-aminoantipyrine | 0.003–0.03% |
| phenol derivative, aniline derivative, or naphthol derivative | 0.03–0.3% |
| EDTA-2Na | 0.01–100 mmole/l |

*e.g. phosphate buffer, tris buffer, Good's buffer, etc. The generated $H_2O_2$ is measured quantitatively.

[Measurement of Glycerol]

$$\text{glycerol} + \text{NAD} \xrightarrow{\text{glycerol dehydrogenase}} \text{dihydroxyacetone} + \text{NADH} + H^+$$

$$\text{NADH} + \tfrac{1}{2} O_2 \xrightarrow{\frac{Mn^{2+} \text{ or } Co^{2+}}{\text{peroxidase}}} \text{NAD} + \tfrac{1}{2} H_2O_2$$

(i) The case of using $Mn^{2+}$
Reagent:
| | |
|---|---|
| buffer solution* (pH 7–9) | 3 ml |
| $MnCl_2\cdot 4H_2O$ | 0.1–100 mmole/l |
| peroxidase | 500–20000 units/l |
| glycerol dehydrogenase | 100–1000 units/l |
| NAD | 0.2–2 g/l |
| 4-aminoantipyrine | 0.003–0.03% |
| phenol derivative, aniline derivative, or naphthol derivative | 0.03–0.3% |
| EDTA-2Na | 0.1–100 mmole/l |

(ii) The case of using $Co^{2+}$
First reagent:
| | |
|---|---|
| buffer solution* (pH 7.5–9) | 0.5 ml |
| NAD | 0.2–2 g/l |
| glycerol dehydrogenase | 100–1000 units/l |

Second reagent:
| | |
|---|---|
| buffer solution* (pH 6–8) | 3 ml |
| $CoCl_2\cdot 6H_2O$ | 1–200 mmole/l |
| peroxidase | 500–20000 units/l |
| 4-aminoantipyrine | 0.003–0.03% |

[Measurement of Glycerol] -continued

| | |
|---|---|
| phenol derivative, aniline derivative, or naphthol derivative | 0.03–0.3% |
| EDTA-2Na | 0.1–100 mmole/l |

*e.g. phosphate buffer, tris buffer, Good's buffer, etc. The generated $H_2O_2$ is measured quantitatively.

[Measurement of Glycerol-3-phosphate]

$$\text{glycerol-3-phosphate} + \text{NAD} \xrightleftharpoons{\text{glycerol-3-phosphate dehydrogenase}} \text{dihydroxyacetone-phosphate} + \text{NADH} + H^+$$

$$\text{NADH} + \tfrac{1}{2} O_2 \xrightarrow{\frac{Mn^{2+} \text{ or } Co^{2+}}{\text{peroxidase}}} \text{NAD} + \tfrac{1}{2} H_2O_2$$

Reagent:
| | |
|---|---|
| buffer solution* (pH 7–9) | 3 ml |
| $MnCl_2\cdot 4H_2O$ or | 0.1–100 mmole/l |
| $CoCl_2\cdot 6H_2O$ | 1–200 mmole/l |
| peroxidase | 500–20000 units/l |
| glycerol-3-phosphate dehydrogenase | 1000–10000 units/l |
| NAD | 0.2–2 g/l |
| 4-aminoantipyrine | 0.003–0.03% |
| phenol derivative, aniline derivative, or naphthol derivative | 0.03–0.3% |
| EDTA-2Na | 0.1–100 mmole/l |

*e.g. phosphate buffer, tris buffer, Good's buffer, etc. The generated $H_2O_2$ is measured quantitatively.

[Measurement of Glucose-6-phosphate]

$$\text{D-glucose-6-phosphate} + \text{NADP} \xrightleftharpoons{\text{glucose-6-phosphate dehydrogenase}} \text{D-glucono-}\delta\text{-lactone-6-phosphate} + \text{NADPH} + H^+$$

$$\text{NADPH} + \tfrac{1}{2} O_2 \xrightarrow{\frac{Mn^{2+} \text{ or } Co^{2+}}{\text{peroxidase}}} \text{NADP} + \tfrac{1}{2} H_2O_2$$

First reagent:
| | |
|---|---|
| buffer solution* (pH 7.5–9) | 0.5 ml |
| NAD | 0.2–2 g/l |
| glucose-6-phosphate dehydrogenase | 100–1000 units/l |

Second reagent:
| | |
|---|---|
| buffer solution* (pH 6–8) | 3 ml |
| $MnCl_2\cdot 4H_2O$ or | 0.1–100 mmole/l |
| $CoCl_2\cdot 6H_2O$ | 1–200 mmole/l |
| peroxidase | 500–20000 units/l |
| 4-aminoantipyrine | 0.003–0.03% |
| phenol derivative, aniline derivative, or naphthol derivative | 0.03–0.3% |

| -continued | |
|---|---|
| [Measurement of Glucose-6-phosphate] | |
| EDTA-2Na | 0.1–100 mmole/l |

*e.g. phosphate buffer, tris buffer, Good's buffer, etc. The generated $H_2O_2$ is measured quantitatively.

[Measurement of Aldehyde]

$$NAD(P)H + \tfrac{1}{2} O_2 \xrightarrow[\text{peroxidase}]{Mn^{2+} \text{ or } Co^{2+}} NAD(P) + \tfrac{1}{2} H_2O_2$$

| First reagent: | |
|---|---|
| buffer solution* (pH 7.5–9) | 0.5 ml |
| NAD | 0.2–2 g/l |
| aldehyde dehydrogenase | 100–1000 units/l |
| Second reagent: | |
| buffer solution* (pH 6–8) | 3 ml |
| $MnCl_2.4H_2O$ or | 0.1–100 mmole/l |
| $CoCl_2.6H_2O$ | 1–200 mmole/l |
| peroxidase | 500–20000 units/l |
| 4-aminoantipyrine | 0.003–0.03% |
| phenol derivative, aniline derivative, or naphthol derivative | 0.03–0.3% |
| EDTA-2Na | 0.1–100 mmole/l |

*e.g. phosphate buffer, tris buffer, Good's buffer, etc. The generated $H_2O_2$ is measured quantitatively.

According to the process of this invention, body fluid components such as in serum, urine, etc., e.g., cholesterol, triglyceride, glucose, formaldehyde, aldehyde, bile acids, can be measured quantitatively by using enzymatic reactions; activities of dehydrogenases which act specifically on substrates to produce reduced form coenzymes can be measured; the amounts and activities of substrates, coenzymes, enzymes, these having relations to enzymatic reactions which can be connected to such enzymatic reactions, can be measured easily and effectively. Therefore, the process of this invention contributes greatly to this art.

This invention is illustrated by way of the following Examples, in which all percents are by weight unless otherwise specified.

EXAMPLE 1

Determination of NADH

A color reagent was prepared by dissolving 10 mmole/l of $MnCl_2.4H_2O$, 0.1% of phenol, 0.01% of 4-aminoantipyrine, and 6000 units/l of peroxidase in 0.05M tris-HCl buffer solution (pH 7.4).

NADH was dissolved in 0.05M tris-HCl buffer solution (pH 7.4) so as to make standard solutions having the concentration of 1, 2, 3, 4, 5 and 6 g/l, respectively.

To 50 μl of a standard solution, 3 ml of the color reagent was added and incubated at 37° C. for 10 minutes. Absorbance at the wavelength of 505 nm was measured by using reagent blank as control.

Figure 1:
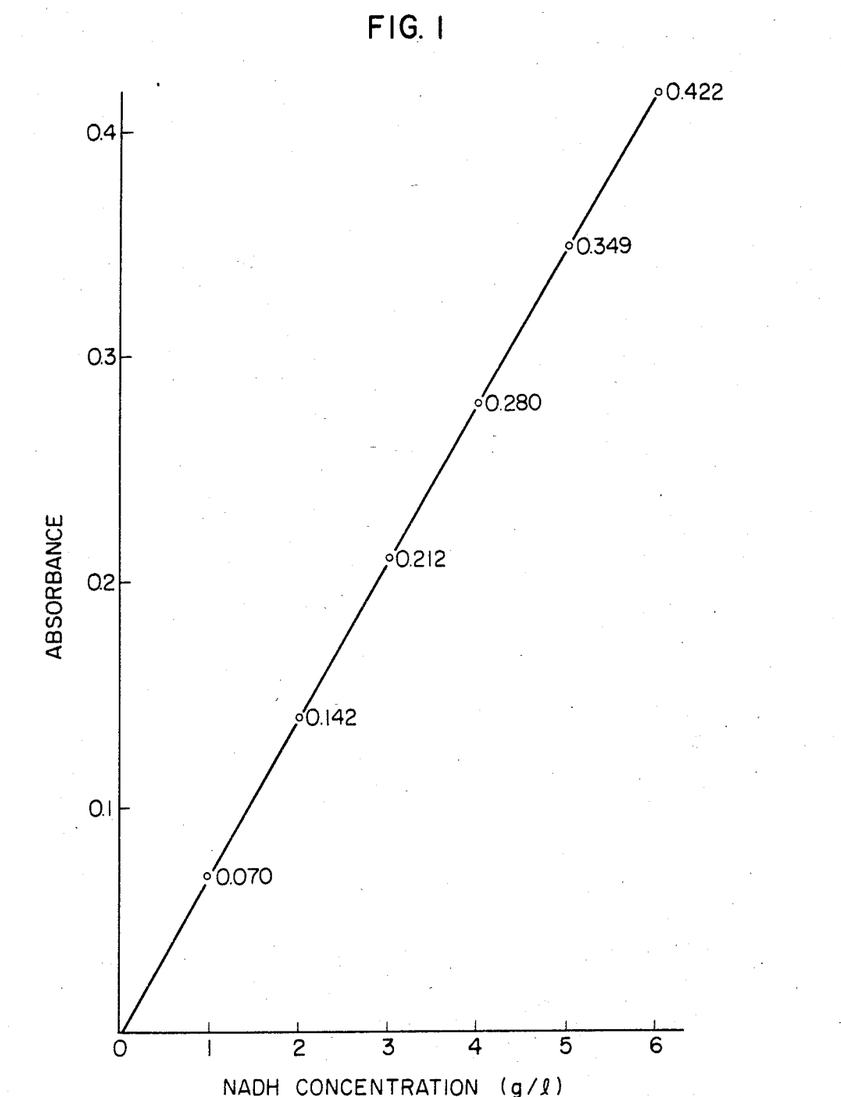
FIGS. 1 to 3 are graphs showing calibration curves for NADH concentration.

The calibration curve as shown in FIG. 1 was obtained when absorbances at different NADH concentrations (g/l) were plotted and lined. The calibration curve is a straight line started from the origin and shows good quantitativeness.

EXAMPLE 2

Determination of NADH

A color reagent was prepared by dissolving 10 mmole/l of $CoCl_2.6H_2O$, 0.1% of phenol, 0.01% of 4-aminoantipyrine, and 6000 units/l of peroxidase in 0.05M tris-HCl buffer solution (pH 7.4).

The same standard solutions as used in Example 1 were used.

To 50 μl of a standard solution, 3 ml of the color reagent was added and incubated at 37° C. for 10 minutes. Absorbance at the wavelength of 505 nm was measured by using reagent blank as control.

Figure 2:
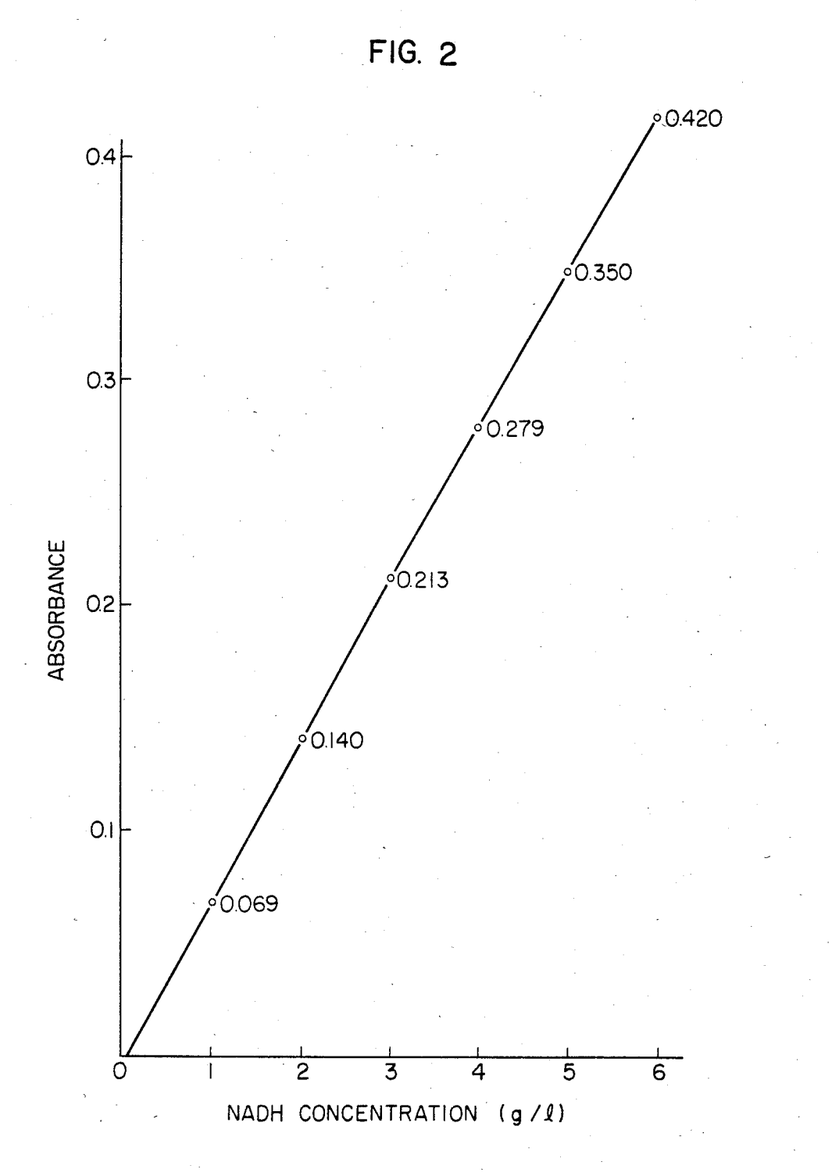

The calibration curve as shown in FIG. 2 was obtained when absorbances at different NADH concentrations (g/l) were plotted and lined. The calibration curve is a straight line started from the origin and shows good quantitativeness.

EXAMPLE 3

Determination of NADH (Double reagent process)

A first reagent was prepared by dissolving 25 mmole/l of $MnCl_2.4H_2O$ in 0.05M tris-HCl buffer solution (pH 7.5).

A second reagent was prepared by dissolving 0.1% of phenol, 0.01% of 4-aminoantipyrine, and 6000 units/l of peroxidase in 0.05M tris-HCl buffer solution.

The same standard solutions as used in Example 1 were used.

To 50 μl of a standard solution, 1 ml of the first solution was added and incubated at 37° C. for 5 minutes, and then 3 ml of the second reagent was added and incubated at 37° C. for 10 minutes. Absorbance at the wavelength of 505 nm was measured by using reagent blank as control.

Figure 3:
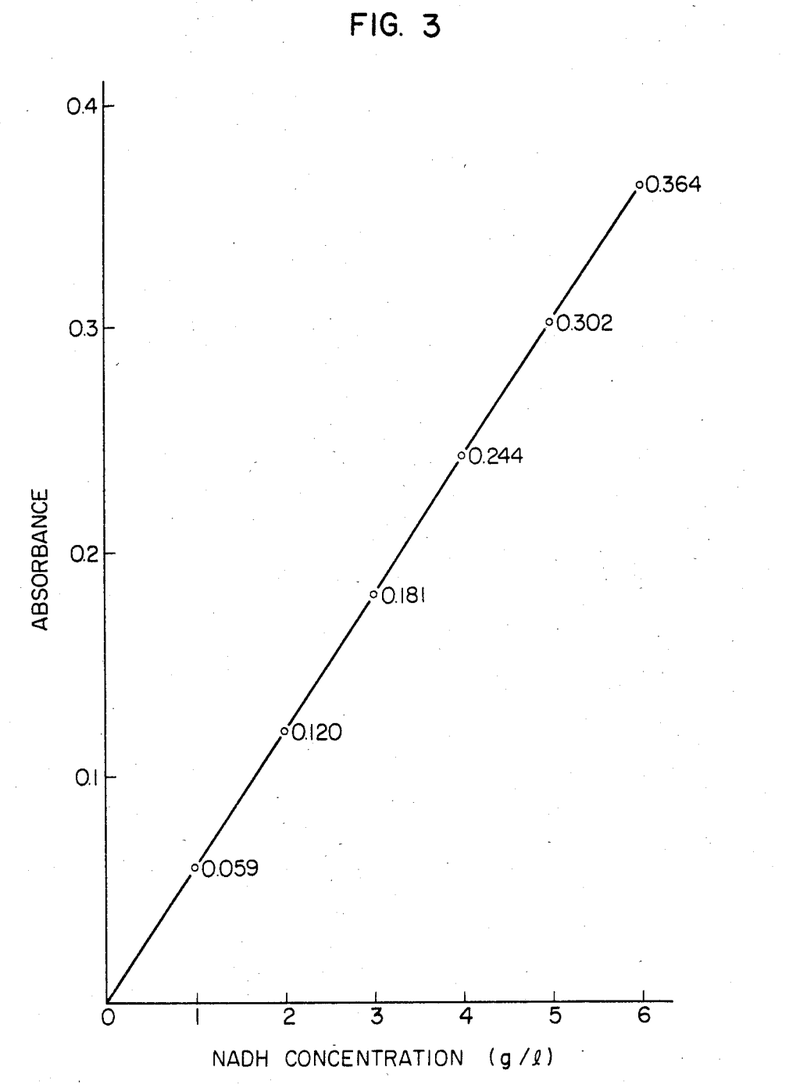

The calibration curve as shown in FIG. 3 was obtained when absorbances at different NADH concentrations (g/l) were plotted and lined. The calibration curve is a straight line started from the origin and shows good quantitativeness.

EXAMPLE 4

Measurement of LDH Activity

A substrate buffer solution was prepared by dissolving 1 g/l of NAD, and 0.05 mole/l of L-lactic acid in 0.1M tris-HCl buffer solution (pH 8.35).

A color reagent was prepared by dissolving 2.5 mmole/l of $MnCl_2.4H_2O$, 1 g/l of N-ethyl-N-(β-hydroxyethyl)-m-toluidine, 0.1 g/l of 4-aminoantipyrine, and 6000 units/l of peroxidase in 0.1M tris-HCl buffer solution (pH 5.7).

To 50 μl of serum sample, 0.5 ml of the substrate buffer solution pre-heated at 37° C. was added and incubated at 37° C. for 10 minutes and then 3 ml of the color reagent was added and incubated at 37° C. for 10 minutes. Absorbance at the wavelength of 505 nm was measured by using reagent blank as control.

Figure 4:
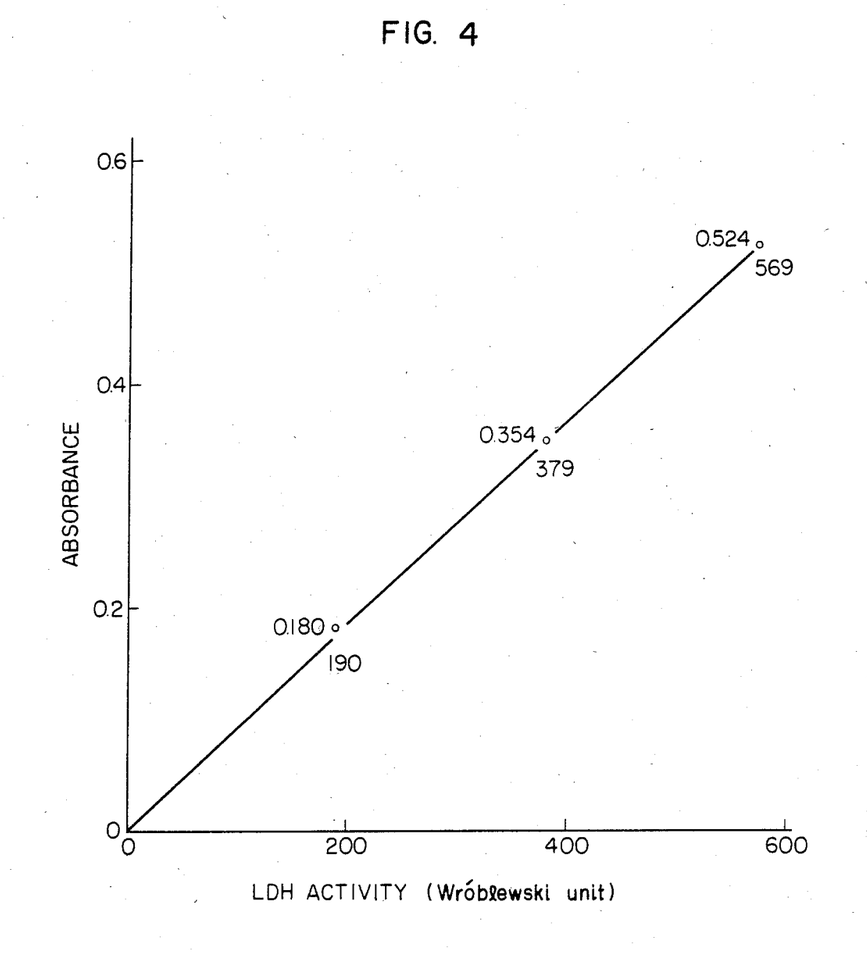
FIG. 4 is a graph showing a calibration curve for LDH activity.

Using standard serum of known LDH activity, the calibration curve as shown in FIG. 4 was obtained in the same manner as the serum sample. LDH activity in a serum sample can be obtained by using the calibration curve of FIG. 4.

REFERENCE EXAMPLE 1

Measurement of LDH Activity (Prior Art Method)

A substrate-color reagent was prepared by dissolving 1 g/l of NAD, 0.05 mole/l of L-lactic acid, 0.05% of Triton X-100 (octyl phenoxy polyethoxyethanol-available from Rohm and Haas Company), 400 mg/l of nitrotetrazolium blue, and 2000 units/l of diaphorase in 0.1M tris-HCl buffer solution (pH 8.0).

To 50 $\mu$l of serum sample, 0.5 ml of the substrate-color reagent pre-heated at 37° C. was added and incubated at 37° C. for 10 minutes. Then, 5.0 ml of 0.1N HCl was added and mixed well. Absorbance at the wavelength of 560 nm was measured using reagent blank as control.

Using standard serum of known LDH activity, the calibration curve was obtained in the same manner as the serum sample. LDH activity in a serum sample can be obtained by using the calibration curve.

The results obtained as mentioned above are shown in Table 1.

TABLE 1

| Serum No. | Example 4 (X) | Reference Example 1 (Y) |
|---|---|---|
| 1 | 223* | 223* |
| 2 | 201 | 190 |
| 3 | 224 | 208 |
| 4 | 276 | 289 |
| 5 | 256 | 264 |
| 6 | 316 | 328 |
| 7 | 248 | 249 |
| 8 | 202 | 198 |
| 9 | 253 | 260 |
| 10 | 362 | 355 |
| 11 | 158 | 162 |
| 12 | 176 | 187 |
| Average | 241.3 | 242.8 |
| SD | 57.8 | 59.4 |

Note
*Wroblewski unit
$\gamma = 0.987$
$Y = 1.04X - 8.3$

As shown in Table 1, the values of Example 4 are in good agreement with those of Reference Example 1 and there is no significant difference between the two.

In the case of Reference Example 1 wherein nitrotetrazolium blue was used, staining of cuvettes and tubes was admitted, but there was admitted no staining in the process of this invention.

EXAMPLE 5

Measurement of Concentration of Sodium Glycocholate

A color reagent was prepared by dissolving 150 units/l of 3α-hydroxysteroid dehydrogenase, 400 mg/l of NAD, 6000 units/l of peroxidase, 2.5 mmole/l of MnCl$_2$, 1.2 g/l of EDTA.4Na (sodium edetate) and 0.1 mmole/l of bis(p-diethylaminophenyl)-2-sulfophenyl methane sodium salt and 0.5 g/l of β-cyclodextrin in 0.1M tris-HCl buffer solution (pH 7.5).

To each 200 $\mu$l of an aqueous solution of sodium glycocholate of different concentration (50, 100, 150 and 200 $\mu$mole/l), 3 ml of the color reagent was added and incubated at 37° C. for 20 minutes. Absorbance at the wavelength of 620 nm was measured using reagent blank as control.

Figure 5:
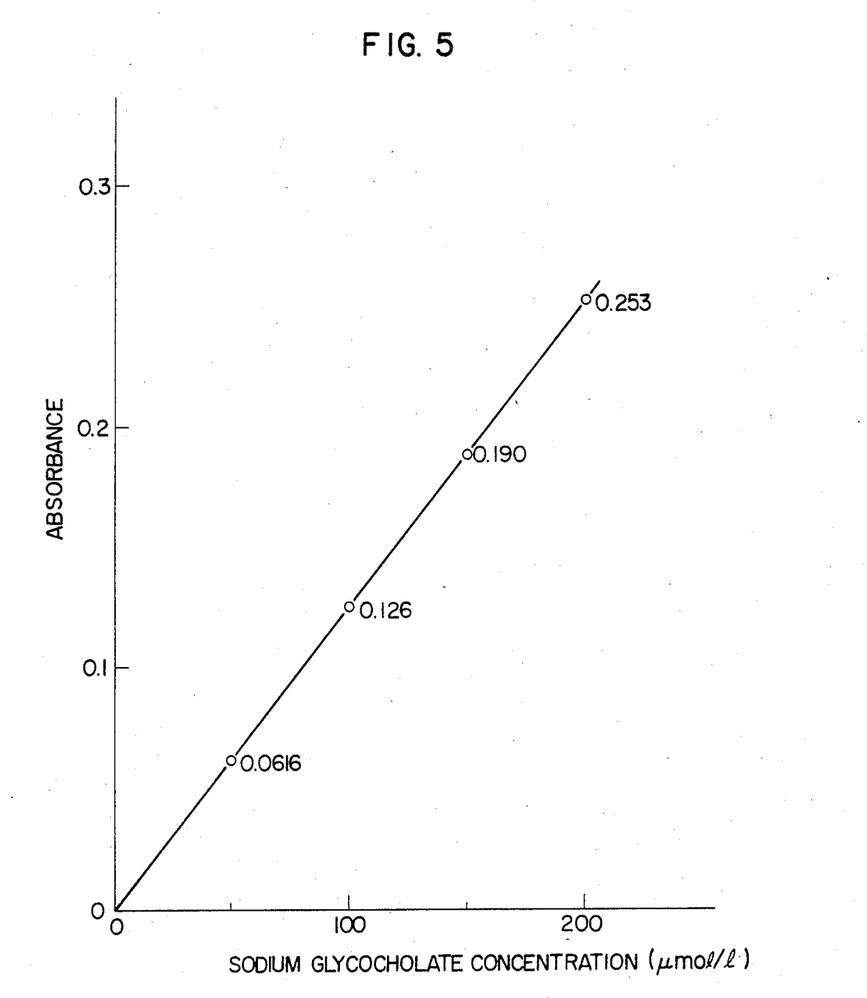
FIG. 5 is a graph showing a calibration curve for sodium glycocholate concentration.

The calibration curve as shown in FIG. 5 was obtained when absorbances at different concentrations of sodium glycocholate ($\mu$mole/l) were plotted and lined.

The calibration curve is a straight line started from the origin and shows good quantitativeness.

EXAMPLE 6

Determination of Free Cholesterol in Serum

A color reagent was prepared by dissolving 5 mmole/l of MnCl$_2$.4H$_2$O, 0.1% of phenol, 0.01% of 4-aminoantipyrine, 6000 units/l of peroxidase, 700 units/l of cholesterol dehydrogenase, 0.12% of EDTA-2Na (disodium edetate), 350 mg/l of NAD, and 0.07% of Triton X-100 in 0.05M tris-HCl buffer solution (pH 7.5).

To 50 $\mu$l of serum sample, 3 ml of the color reagent was added and incubated at 37° C. for 20 minutes. Absorbance at the wavelength of 505 nm was measured using reagent blank as control.

Using a standard solution containing cholesterol in an amount of 1 g/l, the absorbance was measured in the same manner as the serum sample. The free cholesterol concentration in the serum sample was calculated from the absorbances.

REFERENCE EXAMPLE 2

Determination of Free Cholesterol in Serum

A color reagent was prepared by dissolving 0.1% phenol, 0.01% of 4-aminoantipyrine, 100 units/l of cholesterol oxidase, 3000 units/l of peroxidase, and 0.15% of Triton X-100 in 0.1M phosphate buffer solution (pH 7.0).

To 50 $\mu$l of serum sample, 3 ml of the color reagent was added and incubated at 37° C. for 15 minutes. Absorbance at the wavelength of 505 nm was measured using reagent blank as control. Using a standard solution containing cholesterol in an amount of 1 g/l, the absorbance was measured in the same manner as the serum sample. The free cholesterol concentration in the serum sample was calculated from the absorbances.

The results obtained as mentioned above are shown in Table 2.

TABLE 2

| Serum No. | Example 6 (X) | Reference Example 2 (Y) |
|---|---|---|
| 1 | 400 mg/l | 380 mg/l |
| 2 | 430 | 420 |
| 3 | 520 | 500 |
| 4 | 400 | 390 |
| 5 | 540 | 570 |
| 6 | 480 | 460 |
| 7 | 600 | 620 |
| 8 | 440 | 440 |
| 9 | 380 | 410 |
| 10 | 310 | 330 |
| Average | 450 | 452 |
| SD | 85.9 | 89.0 |

Note
$\gamma = 0.972$,
$Y = 1.01X - 1.4$

As shown in Table 2, the values of Example 6 are in good agreement with those of Reference Example 2 and there is no significant difference between the two.

EXAMPLE 7

Determination of Free Cholesterol in Serum

A color reagent was prepared by dissolving 5 mmole/l of CoCl$_2$.6H$_2$O, 0.1% of phenol, 0.01% of 4-aminoantipyrine, 6000 units/l of peroxidase, 700 units/l of cholesterol dehydrogenase, 0.12% of EDTA-2Na, 350 mg/l of NAD, and 0.07% of Triton X-100 in 0.05M tris-HCl buffer solution (pH 7.5).

To 50 μl of serum sample, 3 ml of the color reagent was added and incubated at 37° C. for 20 minutes. Absorbance at the wavelength of 505 nm was measured using reagent blank as control.

Using a standard solution containing cholesterol in an amount of 1 g/l, the absorbance was measured in the same manner as the serum sample. The free cholesterol concentration in the serum sample was calculated from the absorbances.

REFERENCE EXAMPLE 3

Determination of Free Cholesterol in Serum

The procedures of Reference Example 2 were repeated.

The results obtained as mentioned above are shown in Table 3.

TABLE 3

| Serum No. | Example 7 (X) | Reference Example 3 (Y) |
|---|---|---|
| 1 | 450 mg/l | 430 mg/l |
| 2 | 430 | 440 |
| 3 | 370 | 390 |
| 4 | 390 | 390 |
| 5 | 690 | 700 |
| 6 | 540 | 540 |
| 7 | 630 | 620 |
| 8 | 320 | 330 |
| 9 | 530 | 530 |
| 10 | 540 | 550 |
| Average | 489 | 492 |
| SD | 117.7 | 115.6 |

Note
$\gamma = 0.995$,
$Y = 0.98X + 13.9$

As shown in Table 3, the values of Example 7 are in good agreement with those of Reference Example 3 and there is no significant difference between the two.

What is claimed is:

1. A process for determining a reduced form coenzyme, NADH or NADPH, which comprises acting a peroxidase on a reduced form coenzyme in the presence of $Mn^{2+}$ or $Co^{2+}$ metal ions in the range of about 0.1 m mole/l. to 200 m mole/l., to generate hydrogen peroxide, and measuring the amount of hydrogen peroxide colorimetrically.

2. A process according to claim 1, wherein the reduced form coenzyme is obtained by acting a dehydrogenase on a substrate in the presence of a coenzyme.

3. A process according to claim 2, wherein the substrate is lactic acid, the dehydrogenase is lactate dehydrogenase, and the coenzyme is nicotinamide adenine dinucleotide or nicotinamide adenine dinucleotidephosphate.

4. A process according to claim 2, wherein the substrate is α-hydroxybutyric acid, the dehydrogenase is α-hydroxybutyrate dehydrogenase, and the coenzyme is nicotinamide adenine dinucleotide or nicotinamide adenine dinucleotidephosphate.

5. A process according to claim 2, wherein the substrate is cholesterol, the dehydrogenase is cholesterol dehydrogenase, and the coenzyme is nicotinamide adenine dinucleotide or nicotinamide adenine dinucleotidephosphate.

6. A process according to claim 2, wherein the substrate is bile acids, the dehydrogenase is 3α-hydroxysteroid dehydrogenase, and the coenzyme is nicotinamide adenine dinucleotide or nicotinamide adenine dinucleotidephosphate.

7. A process according to claim 2, wherein the substrate is glycerol or aldehyde, the dehydrogenase is glycerol dehydrogenase or aldehyde dehydrogenase, and the coenzyme is nicotinamide adenine dinucleotide or nicotinamide adenine dinucleotidephosphate.

8. A process according to claim 2, wherein the substrate is glycerol-3-phosphate or glucose-6-phosphate, the dehydrogenase is glycerol-3-phosphate dehydrogenase or glucose-6-phosphate dehydrogenase, and the coenzyme is nicotinamide adenine dinucleotide or nicotinamide adenine dinucleotidephosphate.

9. A process for determining a reduced form coenzyme, NADH or NADPH, which comprises adding to a sample to be tested a mixture comprising divalent manganese or cobalt ions in the range of about 0.1 m mole/l. to 200 m mole/l., a peroxidase, and redox color reagent or reagents, incubating the resulting mixture to produce a color, and measuring the absorbance of the color produced.

10. A process for determining a reduced form coenzyme, NADH or NADPH, which comprises adding to a sample to be tested a first solution comprising divalent manganese or cobalt ions in the range of about 0.1 m mole/l. to 200 m mole/l., and redox color reagent or reagents, incubating the resulting mixture, adding to the resulting mixture a second solution comprising peroxidase, incubating the resulting mixture to produce a color, and measuring the absorbance of the color produced.

11. A process for determining a reduced form coenzyme, NADH or NADPH, which is obtained by reacting a dehydrogenase on a suitable substrate in the presence of a coenzyme, said process comprising adding to a sample to be tested a first solution comprising a substrate, a dehydrogenase, and a coenzyme, followed by incubation, adding to the resulting mixture a second solution comprising divalent manganese or cobalt ions in the range of about 0.1 m mole/l. to 200 m mole/l., redox color reagent or reagents, and a peroxidase, followed by incubation to produce a color, and measuring the absorbance of the color produced.

12. A process for determining a reduced form coenzyme, NADH or NADPH, which is obtained by reacting a dehydrogenase on a suitable substrate in the presences of a coenzyme, said process comprising adding to a sample to be tested a mixture comprising a substrate, a dehydrogenase, a coenzyme, divalent manganese or cobalt ions in the range of about 0.1 m mole/l. to 200 m mole/l., a peroxidase, and redox color reagent or reagents, incubating the resulting mixture to produce a color, and measuring the absorbance of the color produced.

* * * * *